(12) United States Patent
Granchelli et al.

(10) Patent No.: US 8,642,307 B2
(45) Date of Patent: Feb. 4, 2014

(54) CELL CULTURE SURFACE CHEMISTRIES

(75) Inventors: Joesph Granchelli, New York, NY (US); Thomas Cummins, Penfield, NY (US)

(73) Assignee: Nalge Nunc International Corporation, Rochester, NY (US)

( * ) Notice: Subject to any disclaimer, the term of this patent is extended or adjusted under 35 U.S.C. 154(b) by 1652 days.

(21) Appl. No.: 11/420,267

(22) Filed: May 25, 2006

(65) Prior Publication Data

US 2007/0275457 A1  Nov. 29, 2007

(51) Int. Cl.
*C12N 11/08* (2006.01)
*C12M 3/00* (2006.01)

(52) U.S. Cl.
USPC ......... 435/180; 435/174; 435/325; 435/289.1

(58) Field of Classification Search
USPC ............... 435/174, 180, 325, 289.1
See application file for complete search history.

(56) References Cited

U.S. PATENT DOCUMENTS

| | | | |
|---|---|---|---|
| 3,899,563 A | 8/1975 | Oxenrider et al. | |
| 4,254,180 A | 3/1981 | Kline | |
| 4,415,668 A | 11/1983 | Siegel | |
| 5,041,266 A * | 8/1991 | Fox | 422/102 |
| 5,236,962 A * | 8/1993 | Govoni et al. | 521/56 |
| 5,266,476 A * | 11/1993 | Sussman et al. | 435/399 |
| 5,512,474 A | 4/1996 | Clapper | |
| 5,514,581 A | 5/1996 | Ferrari et al. | |
| 5,589,563 A | 12/1996 | Ward et al. | |
| 5,723,588 A | 3/1998 | Donofrio et al. | |
| 5,756,632 A | 5/1998 | Ward | |
| 5,808,012 A | 9/1998 | Donofrio et al. | |
| 5,858,503 A * | 1/1999 | Everhart et al. | 428/131 |
| 5,972,475 A * | 10/1999 | Beekman | 428/167 |
| 6,177,282 B1 | 1/2001 | McIntyre | |
| 6,342,591 B1 | 1/2002 | Zamora et al. | |
| 6,448,305 B1 | 9/2002 | Watterson, III et al. | |
| 6,576,705 B1 | 6/2003 | Maillet et al. | |
| 7,220,334 B2 * | 5/2007 | Anazawa et al. | 156/235 |
| 7,601,367 B2 * | 10/2009 | Monahan et al. | 424/450 |
| 2002/0173033 A1 * | 11/2002 | Hammerick et al. | 435/305.2 |
| 2002/0177120 A1 * | 11/2002 | Elliott et al. | 435/4 |
| 2003/0134100 A1 * | 7/2003 | Mao et al. | 428/304.4 |
| 2005/0238620 A1 * | 10/2005 | Gomer et al. | 424/85.2 |
| 2006/0188487 A1 * | 8/2006 | Thomas et al. | 424/93.7 |
| 2007/0202589 A1 * | 8/2007 | Kikuchi et al. | 435/293.1 |
| 2007/0207540 A1 * | 9/2007 | Akashi et al. | 435/325 |
| 2008/0194420 A1 * | 8/2008 | Schmid et al. | 506/9 |

FOREIGN PATENT DOCUMENTS

| | | |
|---|---|---|
| EP | 1489167 A1 | 12/2004 |
| JP | 06181740 A | 7/1994 |
| JP | 08173144 A | 7/1996 |
| JP | 2004331793 A | 11/2004 |
| WO | WO 2004-044012 A1 | 5/2004 |

OTHER PUBLICATIONS

Lenntech Web page www.lenntech.com/polypropylene.htm downloaded Mar. 29, 2009.*
Rawn. J.D. Biochemistry (1983) (Harper & Row: New York, NY), p. 35.*

* cited by examiner

*Primary Examiner* — Susan Hanley
(74) *Attorney, Agent, or Firm* — Wood Herron & Evans, LLP

(57) ABSTRACT

A surface supporting growth of cells in culture, the surface prepare to provide hydrophilic moieties exposed thereon for enhancing the attachment of biological materials. The surface contains the hydrophilic moiety as part of an amphipathic molecule also having a hydrophobic region that is anchored or embedded within a polymer substrate, and oriented such that the hydrophilic moieties are exposed on the outer surface of the substrate. In one embodiment the surface is customized to provide qualitative and quantitative moieties to enhance particular cell growth. In one embodiment, the surface is provided on a culture apparatus such as a dish or plate.

10 Claims, 2 Drawing Sheets

CELL CULTURE SURFACE CHEMISTRIES

FIELD OF THE INVENTION

A method and apparatus to culture cells and other biological materials.

BACKGROUND

The ability to grow and study various biological materials, such as mammalian cells, is important in the laboratory and industry. However, many cells and other biological materials will grow only if they can attach to an appropriate substrate (i.e., the biological material exhibits an adherent phenotype). The ability of many biological materials to attach and grow on a substrate is dependent upon the substrate being chemically activated to be somewhat hydrophilic. Hydrophilicity may be provided by various functional groups on the substrate. These functional groups include hydroxyl (OH), carboxyl (COOH), and amine ($NH_2$ and NH) groups, for example.

Preparing such a chemically activated substrate generally involves (1) the application of energy in the form of discharge of either corona or plasma to the substrate, or (2) the application of a coating (such as poly-D-lysine or collagen) to the substrate. These processes provide groups to which biological materials may attach. For example, in corona discharge, the substrate being treated is exposed to an electrical discharge, or corona. Oxygen molecules within the discharge area break into their atomic form and are free to bond to the ends of molecules of the substrate being treated, resulting in a desired chemically activated substrate. The main advantage of corona or plasma discharge treatment of substrates is ease of manufacture; polymeric substrates subjected to such energetic discharge may be easily treated in-line and sterilized.

However, both corona and plasma discharge treatments have drawbacks. For example, corona discharge is limited to bonding of oxygen within the first few nanometers of the substrate, and can be wiped off. Thus, the substrate can be degraded rapidly. Additionally, corona discharge treatment can generally only provide only up to about 20%, at best, surface oxygen on the substrate. Certain biological materials, such as certain cell lines, require more oxygen. While plasma discharge can produce higher oxygen levels than corona discharge, it requires the substrate to be treated in a vacuum.

Treating substrates by the application of various biologic coatings, such as poly-D-lysine or collagen, mimic the milieu on which cells would typically grow. However, these coatings often do not survive sterilization by gamma irradiation. Additionally, the biological origin of these coatings raises the possibility of disease transmission.

Energetic discharge and coating treatments can provide only a few standard activated substrates for use with all biological materials, producing little variation in the surface chemistry of substrates used to culture biological materials. This is problematic because, to some degree, every cell line or other biological material exhibits a preference for a certain type, mixture, and/or ratio of functional groups on a culture substrate. For example, some exhibit a preference for multiple different functional groups, while some exhibit a preference for only one functional group in a specific concentration range. However, as described above, current technologies generally employ "one-size-fits-all" strategies (e.g., a substrate with corona treatment used for all types of cell lines). The resulting substrates can, at best, be controlled to produce a range of surface chemistry, rather than being able to produce any chemistry. For example, corona treatment, even at low power, has a characteristic surface chemistry that is somewhat dependent upon atmospheric conditions at the time (humidity, temperature, and volatile organics in the air). Ultimately, it generally produces a substrate having a range of oxygen concentrations from between 10%-20%. However, it cannot produce substrates having high oxygen concentrations, nor can it produce substrates including other or additional functional groups, such as amine groups. Such a substrate may not be adequate for a particular biological material that exhibits a preference for high oxygen levels and/or amine groups.

Further, many biological materials are grown in culture apparatus that not only have substrates treated as described above, but may also include serum to enhance growth. For example, the human embryonic kidney (HEK) 293 cell line is increasingly used because it is easy to grow, is genetically stable, has a normal complement of human chromosomes, and incorporates portions of the adenovirus genome that make it amenable for genetic manipulation. Other cell lines exhibiting similar characteristics are PER C6, Vero, BHK-21, and MDCK.

HEK cells can be successfully grown under conditions recommended by the American Type Culture Collection (ATCC) (e.g., in Dulbecco's Modified Eagle's Media (DMEM)+10% fetal bovine serum (FBS)) on standard cell culture substrates (e.g., those subjected to corona treatment). Serum enhances HEK cell growth and as such, it has been included in most cell culture procedures. Recently, however, safety concerns have been raised and it is the single most expensive component of most media formulations. While it is desirable to reduce or eliminate the need for serum altogether, the ability of almost all cell lines, including HEK cells, to grow on corona treated substrates diminishes as the serum concentration is reduced.

Recently, the Corning product CellBIND®, is being offered in all standard cell culture formats. CellBIND® includes a substrate described as supporting growth of adherent cells without serum. It has been suggested that the enhanced ability of CellBIND® to grow HEK cells is primarily a result of its higher quantity of oxygen, specifically hydroxyl groups, relative to corona treated substrates (15% oxygen on CellBIND® vs. 8% oxygen on corona treated substrates) and to a lesser but still significant degree by the amount of carboxylic acids (7% carboxylic acid in CellBIND® vs. 2% carboxylic acid on corona treated substrates). However, CellBIND® does not include other functional groups such as amine groups, and it is not tailored to different preferences that may be exhibited by different biological materials.

Other products and methods are desirable. For example, an apparatus and method to control the chemistry of an adherent substrate without secondary treatment (e.g., corona discharge) and/or to improve the quality of existing secondary treatments would be desirable. Further, an apparatus including functional groups on a polymeric substrate that is not subject to degradation and can be used with reduced serum or without serum would be desirable. Further, a method of preparing an apparatus having a substrate that varies in functional groups, both in type and concentration, in order to tailor the apparatus to a particular biological material would be desirable.

SUMMARY OF THE INVENTION

In one embodiment, an apparatus includes a substrate having hydrophilic moieties exposed thereon for enhancing the attachment of biological materials to the substrate. Each hydrophilic moiety is part of a molecule also having a hydrophobic region that is anchored or embedded within the substrate, and oriented such that the hydrophilic moieties are exposed on the substrate. More specifically, the apparatus has a substrate prepared from a blend of polymer plastic resin and amphipathic molecules. The substrate may be nonfibrous, or alternatively may be prepared with fibrous polymers. As is known to those skilled in the art, amphipathic molecules include hydrophilic and hydrophobic regions. The functional groups of the hydrophilic moieties may include, for example, hydroxyl (OH), carboxyl (COOH), and/or amine ($NH_2$ or NH) groups. The hydrophobic region is embedded within the polymer plastic substrate, and the hydrophilic moieties are exposed on the polymer plastic substrate. In further embodiments, the substrate may optionally be treated with another process, for example, corona or plasma discharge or coating with substances such as poly-D-lysine or collagen.

Another embodiment is a method for preparing an apparatus having a substrate for enhancing attachment of biological materials, wherein the substrate includes molecules with exposed hydrophilic moieties, and a hydrophobic region that is anchored or embedded within the substrate.

Another embodiment is a method of making an apparatus tailored to enhance the attachment and growth of a particular biological material, such as a particular cell population. As described above, to some degree, every cell line has a preference for a certain type or ratio of functional groups, such as OH, COOH, and $NH_2$ or NH. The method includes determining a preferred type of hydrophilic functional group or groups for a particular biological material having an adherent phenotype. At least one amphipathic molecule is selected where the hydrophilic region(s) include the particular functional groups preferred by the selected biological material. The selected amphipathic molecule or molecules is blended with a polymer plastic resin to form a blended resin, and the blended resin is used to prepare a culture apparatus. For example, one can mold an apparatus, such as a Petri dish, from the blended resin. This may be done in the absence of any treatment with corona discharge or plasma discharge, or any coating of the plastic surface. Optionally, corona or plasma discharge or coating of the plastic surface may be performed.

BRIEF DESCRIPTION OF THE DRAWINGS

The accompanying drawings, which are incorporated in and constitute a part of this specification, illustrate embodiments of the invention, and, together with the general description of the invention given above and the detailed description of the embodiments given below, serve to explain the principles of the present invention.

DETAILED DESCRIPTION

An apparatus for the culture of biological material, including a substrate facilitating attachment of biological materials that have an adherent phenotype. The substrate has hydrophilic moieties exposed thereon for enhancing the attachment of cells. Each hydrophilic moiety is part of a molecule also having a hydrophobic region (i.e., an amphipathic molecule) that is anchored or embedded on or within the substrate. The molecule is oriented such that the hydrophilic moieties are exposed on the substrate.

Figure 1:
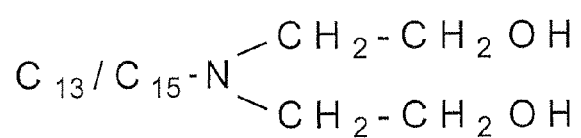
FIG. 1 depicts the structure of alkylamine ethoxylate (Atmer 163), which is an example of an amphipathic molecule that may be used in accordance with the principles of the present invention.

More specifically, the apparatus has a substrate prepared from a blend of polymer plastic resin and amphipathic molecules. This substrate may be nonfibrous, or formed from fibrous polymers. As is known to those skilled in the art, the amphipathic molecules include hydrophilic moieties and a hydrophobic region. The functional groups of the hydrophilic moieties may include, for example, hydroxyl (OH), carboxyl (COOH), and/or amine ($NH_2$ or NH) groups. In specific embodiments, the amphipathic molecules may be chosen from alkylamine ethoxylate (e.g., Atmer 163, Ciba Specialty Chemicals (Tarrytown N.Y.), as shown in FIG. 1), polyethylenimine, octyldecamine, or mixtures thereof. Further, the molecules may include fluoridated groups or compounds. The hydrophobic region is embedded within the polymer plastic substrate, and the hydrophilic moieties are exposed on the polymer plastic substrate. The substrate may optionally be treated with another process, for example, corona or plasma discharge, or coating with substances such as poly-D-lysine or collagen. Optionally, the culture apparatus may or may not be used with serum.

A polystyrene or other resin, used in molding the apparatus, is blended with amphipathic molecules. More specifically, prior to molding any culture apparatus, such as a Petri dish, resin particles of the plastic polymer may be coated with the amphipathic molecules to form the blend, or they may be compounded with the amphipathic molecules to form the blend.

In embodiments where the resin is coated, the amphipathic molecules are blended with the resin pellets at the point of molding. For example, the amphipathic molecules such as can be dissolved in a solvent (such as ethanol) and manually mixed with the resin (for example, polystyrene pellets). Other solvents would include, for example, isopropyl alcohol. Alternatively, a blender may be used. The blender may include a weigh pan to meter out a predetermined amount of pellets, dispense the correct amount of liquid additive, stir the materials, and dispense them.

Alternatively, in embodiments where the resin is compounded with the amphipathic molecules to result in amphipathic molecules incorporated into the resin, the amphipathic compound (e.g., Atmer 163) is mixed into a resin, such as molten polystyrene, as it is extruded. As the material cools and hardens, it is cut into pellets, which are subsequently used to prepare a culture apparatus. In particular embodiments, the resin may be chosen from polystyrene, polypropylene, glycol-modified polyethylene terephthalate (PETG), polyethylene terephthalate (PET), polycarbonate, or mixtures thereof, for example.

The blended resin (i.e., the plastic resin having amphipathic molecules either coated thereon or compounded therein) is formed into the plastic substrate. This is accomplished by heating the plastic resin so that it begins to flow. The molten plastic resin may then be molded into the desired apparatus, such as a Petri dish, microtiter plate, multiwell plate, or any other desired apparatus. As the resin flows, the amphipathic molecules are free to move within the polymer matrix. Referring to FIG. 1, Atmer 163 is one example of an amphipathic molecule that may be used. Atmer 163 is a long chain synthetic hydrocarbon with two hydroxyl (alcohol) functional groups per molecule. Originally designed to impart antistatic properties in a variety of plastics, the long chain portion of the molecule serves as an anchor for the hydroxyl groups. Without being bound to any theory, the resin and amphipathic compounds are incompatible, and the amphipathic compound is relatively small and thus should have some mobility in the polystyrene matrix. Some of the amphipathic material should thus bloom onto the surface. A bloom is a thin coating of an ingredient of a rubber or plastic mixture that migrates to the surface, usually within a few hours after curing or setting. Blooming is a chemical phenomenon that occurs in both plastics and biological systems. The driving force for blooming in both cases is thermodynamic; it is more favorable for molecules of similar structure to interact with each other than it is favorable for more dissimilar molecules to interact. Molecules will also tend to orient themselves to allow like regions of adjacent molecules to interact. In plastics, blooming of slip agents (i.e., bis-stearamide and zinc stearate) aids in the release of parts from the surface of a mold. As is known to those skilled in the art, slip agents are materials either coated or compounded into resin pellets that facilitate the release of the molded part from the mold or prevent static from building up. Such static may build up as pellets are delivered to the point of molding, for example, as pellets are vacuumed through an overhead system of pipes that deliver them to a molding machine from a large silo usually outside a plant.

Figure 2:
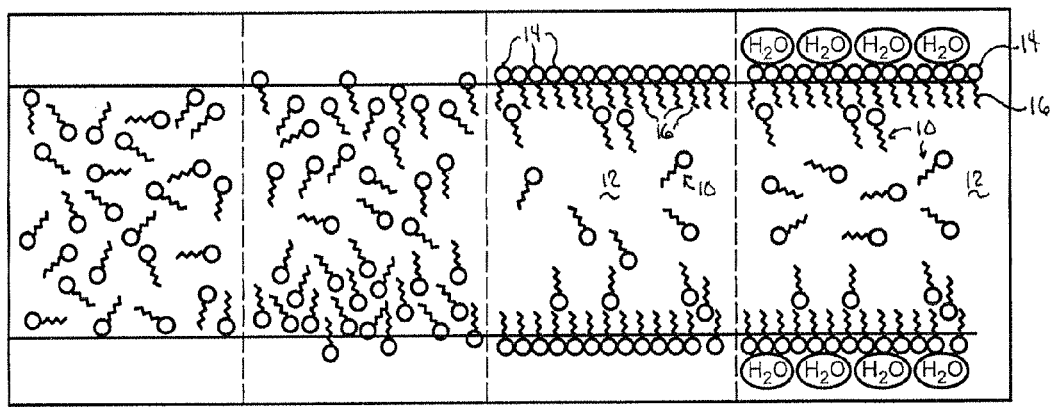
FIG. 2 is a schematic, depicting "blooming" of an amphipathic molecule relative to a polymer plastic substrate.

In particular, and referring to FIG. 2, the amphipathic molecules 10 move through the hydrophobic polymer matrix 12 to orient the hydrophilic moieties 14 on the outer surface of the hydrophobic polymer matrix 12 that forms the substrate. Because the polymer matrix 12 is hydrophobic, the hydrophilic regions 14 become oriented to the outer surface of the hydrophobic polymer matrix, while the hydrophobic regions 16 remain associated with the hydrophobic polymer matrix 12. Thus, the substrate may be heated to increase the mobility of the amphipathic molecules within the polymer matrix. Further, timing may be an issue in preparing an apparatus, because extending the duration during which the amphipathic molecules can move, provides more hydrophilic regions exposure at the outer surface of the apparatus. Thus, the concentration of hydrophilic groups at the outer surface of the substrate can be increased by increasing the duration of the flow of the plastic resin.

The migration of amphipathic molecules, such as Atmer 163, within the substrate is affected, like other diffusional mechanisms, by: (1) the polarity of the molecule in relation to its polymer matrix (incompatibility); the more dissimilar, the faster the bloom rate; (2) crystallinity of the polymer; the more crystalline the slower the bloom rate (polystyrene is crystalline); (3) presence of other additives that sequester or bind the amphipathic compound; (4) concentration; the higher the concentration, the greater the bloom rate; and (5) temperature (mobility); the higher the temperature, the faster the bloom rate.

Amphipathic molecules may be chosen having hydrophobic regions of varying lengths. The hydrophobic region provides an anchor region to become embedded in the cell culture plastic substrate, once it is molded. Thus, the hydrophobic region may be a chain of carbon-linked atoms having a length between about 10 to about 30 carbon atoms, for example. Examples of such molecules include stearic and palmitic acid.

As described above, the hydrophilic moieties of the amphipathic molecules may be chosen from hydroxyls, carboxyls, amines, or mixtures thereof. The exact hydrophilic moieties may be determined based on the particular biological material for which one desires to prepare a culture apparatus. As previously disclosed, certain cell populations may require a particular type, ratio, and/or concentration of a certain functional group or groups on the substrate for optimal adherence and growth. Thus, as nonlimiting examples, one may prepare a substrate that is saturated solely with hydroxyl functional groups for a particular biological material, or may prepare a substrate exhibiting 70% coverage of a 50/50 ratio of hydroxyl and carboxyl functional groups. These functional groups, and their concentration, are merely exemplary, and those skilled in the art will recognize that the apparatus may include any functional groups in any amounts.

The inclusion of amphipathic molecules in the substrate ameliorates the drawbacks of previous forms of culture apparatus for biological materials of adherent phenotypes: i.e., corona or plasma discharge that can be wiped off, or coatings such as poly-D-lysine, that may not survive sterilization. However, the inventive culture apparatus may also be provided with a secondary surface treatment. Thus, the inventive apparatus may include a substrate that is further treated with an energy discharge process, such as corona discharge or plasma discharge. Alternatively, the inventive apparatus may include a substrate that is further coated with a substance such as poly-D-lysine or collagen.

The apparatus may be used for biological materials having adherent phenotypes. The biological materials may be cells, organelles, subcellular structures, viruses, bacteria, other biomolecules, lipids, nucleic acids, proteins, and/or carbohydrates.

Methods are also disclosed for preparing an apparatus having a substrate for enhancing attachment of biological materials, where the apparatus includes a substrate having molecules with exposed hydrophilic moieties and a hydrophobic region that is anchored or embedded within the substrate.

More specifically, the method is tailored to enhance the attachment and growth of a particular biological material, such as a particular cell population. As described above, to some degree, every cell line has a preference for a certain type or ratio of functional groups, such as OH, COOH, and $NH_2$ or NH. Thus, the method includes determining an optimum hydrophilic functional group or groups in that the particular group or groups facilitate association with a predetermined biological material having an adherent phenotype. An amphipathic molecule or molecules including the particular functional groups preferred by the biological material is selected and blended with a polymer plastic resin to form a blended resin, as is subsequently described. The blended resin is molded into a Petri dish, microtiter plate, multiwell plate, or other culture apparatus. This may be done in the absence of any treatment with corona discharge or plasma discharge, or any coating of the plastic substrate. Optionally, corona or plasma discharge or coating of the plastic substrate may be performed secondarily.

In addition to determining the type of functional group for preparation of the apparatus, the method may also include determining a particular concentration of the hydrophilic functional group that facilitates optimal association with the biological material. Thus, when blending the amphipathic molecules with the polymer plastic resin, the molecules can be blended in a concentration, relative to the polymer plastic resin, that is substantially similar to the concentration determined to facilitate optimal association with the biological material.

As described above, blending the amphipathic molecule with the polymer plastic resin can include coating the polymer plastic resin with the amphipathic molecule. Alternatively, blending the amphipathic molecule with the polymer plastic resin may include compounding the polymer plastic resin with the amphipathic molecule.

The principles of the present invention will be more apparent with reference to the following Examples.

Example 1

Preparation of Coated Resin

A 20-liter carboy was filled with polystyrene pellets and weighed. The weight of the carboy itself was then subtracted from the result in order to obtain the weight of the pellets. Atmer 163 (liquid) was then weighed out in an amount to make 1.0% blend, and added to the pellets about one-third at a time. A second batch was prepared to make a 0.1% blend. The percent Atmer-163 was calculated as weight of Atmer-163/weight of pellets times 100. Thus, for the 1.0% blend, 10 g of Atmer-163 were added to 1 kg of polystyrene pellets. For the 0.1% blend, 1 g of Atmer-163 was added to 1 kg of polystyrene pellets. After each one-third addition of Atmer-163, the pellets were rotated in the carboy or mixed with a power drill and auger until all pellets were evenly coated visually.

Example 2

Preparation of Compounded Resin

Compounded Resins were Mixed inline as the polymer is melted in an extruder. The appropriate weight of pellets and additive were metered into the barrel of the extruder where they are melted. As in Example 1, 1.0% and 0.1% blends were prepared. Thus, for the 1.0% blend, 10 g of Atmer-163 were added to 1 kg of polystyrene pellets. For the 0.1% blend, 1 g of Atmer-163 was added to 1 kg of polystyrene pellets. The barrel of the extruder has a screw that forced the molten material (polystyrene and Atmer-163) toward one end and simultaneously mixed the materials. The polymer mixture solidified as it came out of a small bore at the far end of the extruder and was cut into pellets.

Example 3

Sterile blends of Atmer 163 and polystyrene (coated resin) were tested to determine if an effect on cell yield could be observed. Two blends were prepared by manually blending Atmer 163 into polystyrene to final proportions of 1% (w/w) and 0.1% (w/w), as described above in Example 1. In these blends, the resin was coated with Atmer 163. The blended resins were molded into Petri dishes, and then sterilized. After sterilization, the dishes were evaluated by culturing HEK 293 cells at 1% and 0% v/v serum, and results were compared to dishes with standard corona surface treatment or Corning's CellBIND® apparatus. Comparison was performed using cell yield (raw number of cells retrieved per $cm^2$) or relative cell yield (cell yield relative to CellBIND®). Where dishes having corona treatment were evaluated, corona discharge was applied on a moving conveyor belt moving at 10 cm/sec with 700 watts rotating electrodes at a distance of 23 mm from the belt.

HEK cells obtained from ATCC (Accession No. Crl-1573) were removed from storage in liquid nitrogen, flash thawed at 37° C., and allowed to recover overnight in DMEM+10% FBS in a water-jacketed $CO_2$ incubator at 37° C. and 5% $CO_2$. After 24 hours, the media was changed. Cells were passaged four times before use in this experiment, and frozen cells had been passaged 41 times at ATCC. Thus, the total passage number of the cells was 45 at the time of testing. Cells were seeded at a concentration of about 20,000 cells/$cm^2$ in either 1% or 0% serum. Cells grown at 0% serum in CD 293 media (GIBCO, the cell culture systems division of Invitrogen Corporation, Carlsbad Calif.) were incubated at 37° C. and 8% $CO_2$ as per instructions from GIBCO. Cells grown at 1% serum were incubated in standard conditions of 37° C. and 5% $CO_2$.

After four days, dishes were washed with sterile PBS (without calcium or magnesium) as follows: 1 ml PBS was added to the side of the dish, rocked four times, then aspirated. After washing, 1 ml trypsin was added and allowed to stand for approximately two minutes. After two minutes, dishes were agitated at 1000 RPM on a vortex platform mixer for 5-10 seconds until cells were completely dislodged from the bottom as determined by visual examination. One ml of DMEM with 10% FBS was added to stop trypsinization. One ml of this solution was then removed, added to 4 ml trypan blue, and the cells were then counted in the upper and lower chambers of a hemocytometer.

Substrate treatments (sterilization, corona, and heat) were compared with and without two different concentrations of Atmer (1% or 0.1% w/w) (grams of Atmer/100 of resin pellets). 1% is a high concentration and 0.1% is a low concentration. The concentrations were chosen based on recommended ratios from Uniqema (New Castle Del.), relative to antistatic applications. Enhanced discrimination between groups occurred when cells were grown in serum-free media. The results are shown in Tables 1 and 2. In the Tables, "Nunclon Delta" designates the dishes having standard corona surface treatment. Nunclon® Delta (Nunc A/S, Roskilde, Denmark) is the certificate that is issued if the product passes a certain series of cell culture tests as defined by Nalge Nunc's standard quality system document STP-3004.

TABLE 1

HEK cells grown in serum-free media

|  | Non-Sterile | Sterile |
|---|---|---|
| 1% Atmer | — | 318 |
| 0.1% Atmer | — | 6,887 |
| 0% Atmer | — | 1,218 |
| Nunclon Delta | — | 9,571 |
| CellBIND | — | 35,357 |

— test not performed

TABLE 2

HEK cells grown in media with 1% serum

|  | Non-Sterile | Sterile |
|---|---|---|
| 1% Atmer | 6,696 | 114,583 |
| 0.1% Atmer | 49,107 | 161,990 |
| 0% Atmer | 0 | 61,862 |
| Nunclon Delta | — | 116,848 |
| CellBIND | — | 105,377 |

*cells/sq.cm
— test not performed because samples are not available nonsterile

The effect of sterilization on cell yield in different polystyrene blends was evaluated. Sterilization was via gamma irradiation at a level of between 18 and 30 kiloGrays. Sterilization resulted in increased absolute cell yields and cell yield relative to CellBIND® (cell yield of sample/cell yield of CellBIND®; "RCY") for both raw polystyrene, and for polystyrene blended with Atmer. Blended means the material was incorporated into the polymer either at the mold, or beforehand. Under serum-free conditions, the mean cell yield was 1218±264 cells/cm² for sterilized native (i.e., unaltered) polystyrene. When polystyrene was blended with Atmer at high concentration (i.e., 1% Atmer), the yield of cells on the sterilized polystyrene was 318±142 cells/cm² and at low concentration (i.e., 0.1% Atmer) 6887±536 cells/cm², under serum-free conditions.

There are two concentrations referred to in this Example: serum and Atmer. Two concentrations of Atmer were used in culturing cells in two concentrations of serum. The cell yield for the low concentration Atmer blend (0.1% w/w) was larger than can be accounted for by sterilization alone. The difference in yield between native polystyrene and the high concentration Atmer blend (1.0% w/w) was not statistically significant, however the difference between native polystyrene and the low concentration group Atmer blend was significant (P<0.05). Atmer blended at a concentration of 0.1% w/w of polystyrene had a statistically significant effect on HEK cell yield on polystyrene to which no other treatment but sterilization was given when cells were grown without serum. These data are shown in Tables 1 and 2, above.

HEK cells grown with fetal bovine serum (1% v/v) sterilized, native polystyrene had a cell yield of 61,862 cells/cm², while HEK cells grown with FBS (1%) in sterilized polystyrene blended with Atmer at 1% was 6,696 cells/cm² and at 0.1% was 49,107 cells/cm². These differences were statistically significant (p<0.05). The cell yields were about 50× higher than cell yields serum-free for native polystyrene, 20× higher for the high concentration blend, and about 7× higher for the low concentration blend. The presence of serum had a much greater effect on cell yield for HEK cells grown on native polystyrene than for HEK cells grown on polystyrene blended with Atmer, suggesting there is more than one mechanism for binding cells. HEK cells grown on CellBIND®, in comparison, yielded a mean of 35,357±1929 cells/cm² when grown under serum-free conditions and 105,377±10,000 cells/cm² when grown with serum.

The effects of corona treatment on yield in different polystyrene blends were also evaluated (See Tables 3 and 4).

TABLE 3

HEK cells grown at 1% serum on corona treated blends

|  | Non-Sterile | Sterile |
| --- | --- | --- |
| 1% Atmer | 76,212 | 181,973 |
| 0.1% Atmer | 77,487 | 162,415 |
| 0% Atmer | 0 | 103,104 |

TABLE 4

HEK cells grown serum-free on corona treated blends

|  | Non-Sterile | Sterile |
| --- | --- | --- |
| 1% Atmer | — | 9,566 |
| 0.1% Atmer | — | 30,676 |
| 0% Atmer | — | 9,571 |

Corona treatment was delivered by a rotating head treater at a distance of 23 mm from the bottom of the plate at 700 watts for a treatment time of approximately 8 seconds. Corona treatment resulted in increased yield (i.e., cell growth) for both native polystyrene and for polystyrene blended with Atmer. Under serum-free conditions, the yield of cells on corona treated, sterile, native polystyrene was 9,571±884 cells/cm² compared with 1,218±264 cells/cm² without corona treatment, which was an absolute increase of about 8300 cells/cm² and a relative increase of nearly 8×. When polystyrene was blended with Atmer at high concentration (1%), the yield was 9,566±2182 cells/cm² compared to 318±142 cells/cm² without corona treatment, which was an absolute increase of about 9,200 cells/cm² and a relative change of about 30×. When Atmer was blended with polystyrene at low concentration (0.1%) and corona treated, the yield was 30,676±1846 cells/cm² compared to 6,887±536 cells/cm² without corona treatment, which was an absolute increase of about 24,000 cells/cm² and a relative increase of about 4.5×.

The absolute yield and the magnitude of the increase in yield afforded by corona treatment were larger for either blend of Atmer than for raw polystyrene. The largest relative increase was observed with the highest concentration of Atmer; 30 fold increase for the 1% blends and 4.5 fold increase for the 0.1% blends.

The effect of heating the blended polymers was evaluated. Because blooming is a diffusion-limited process, temperature has a large effect on the rate at which equilibrium is achieved. Under serum-free conditions, surfaces that were heated at 60° C. for 24 hours had higher cell yields than unheated surfaces. The results are shown in Table 5 below.

TABLE 5

HEK cells grown in 0% serum media on blended resin

|  | 1% | 0.10% | 0.00% |
| --- | --- | --- | --- |
| Raw Resin | 0 | 0 | 0 |
| Sterilization | 319 +/− 451 | 6888 +/− 1695 | 1218 +/− 877 |
| *Heat Only | 8992 +/− 2337 | 13074 +/− 1681 | 0 |
| *Corona Only | 9566 +/− 6902 | 30676 +/− 5841 | 9571 +/− 1979 |
| *Heat then Corona | 24617 +/− 4688 | 29656 +/− 5754 | — |
| *Corona Then Heat | 15625 +/− 2792 | 31888 +/− 7914 | — |
| CellBind | 35357 +/− 4315 |  |  |

*Parts were tested sterile by gamma irradiation

When a substrate was prepared from Atmer blended at high concentration (1%), the yield increased from 318±142 cells/cm² to 8992±2337 cells/cm², which was an absolute increase of 8,674 cells/cm² and a relative increase of about 28×. At low concentration (0.1%), the yield of cells grown on surfaces that had been heated was 13,073±1681 cells/cm², while the yield of cells grown on surfaces that had not been heated was 6,887±1659 cells/cm², which was an absolute increase of 6,113 cells/cm² and a relative increase of nearly 2×. The increases were statistically significant (p<0.05).

Heat also affected the yield of corona treated parts under serum free conditions. Further, the order of heating (before or after corona treatment) had an effect. With high concentration blends (1% Atmer), the yield on corona treated substrates was 9,566±6902 cells/cm², when heated before treatment, the yield was 24,617±4688 cells/cm², and when heated after treatment, the yield was 15,625±2792 cells/cm². The yield increased by about 15,000 cells/cm² if heat was applied before treatment and by about 6,000 cells/cm² if heat was applied after treatment for cells grown on surfaces as high concentration blends. For cells grown as low concentration blends, the yield for corona treated substrates was 30,676±5841 cells/cm², when heated before treatment, the yield was 29656±5754 cells/cm², and when heated afterward, the yield was 31888±7914 cells/cm².

There was virtually no effect of heating on the cells grown on low concentration substrates (0.1% Atmer) and a significant effect on the high concentration substrates (1% Atmer).

The difference between the heating sequences was also significant ($p<0.05$). The lower concentration blends were significantly better than higher regardless of the order. The absolute yield for the low concentration substrates, while not affected by heating, was still higher even given the effects of heating on the high concentration substrates.

Thus, improvement in cell yield was observed especially at the lower, 0.1% concentration of Atmer (over Nunclon® Delta), both in the reduced serum and serum-free condition. The yield in serum free media was comparable for some groups to Corning's CellBIND® surface. The data suggested that blending was capable of improving cell yields of adherent cell lines such as HEK 293 cells.

Example 4

Figure 3:
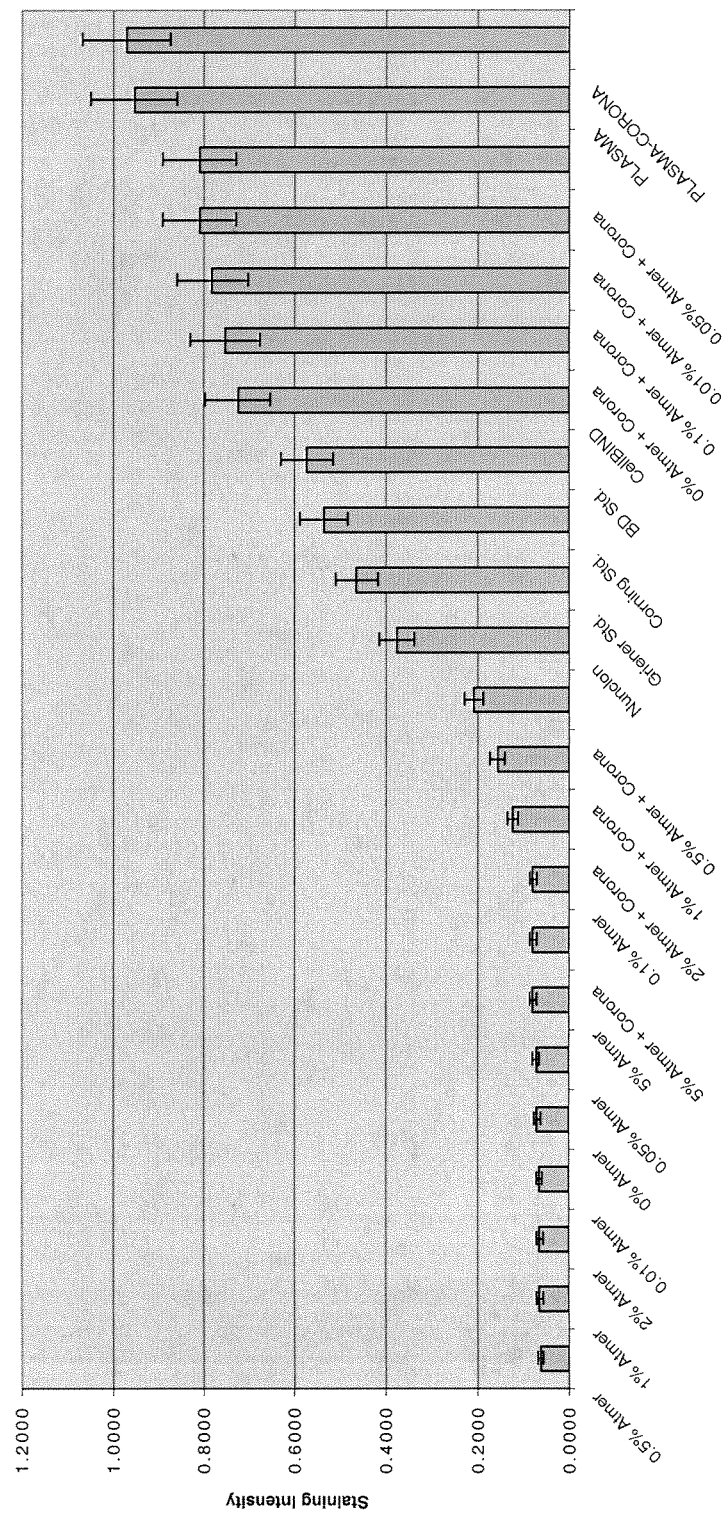
FIG. 3 is a graph showing number of adherent cells in different embodiments of the method.

Sterile blends of Atmer 163 and polystyrene (compounded resin) were tested to determine if an effect on cell yield could be observed. Polystyrene resin was compounded with Atmer-163 to a final concentration of 10% Atmer by Polyvel Inc. (Hammonton, N.J.). The compounded pellets were then metered into normal polystyrene pellets (w/w) to final concentrations of 5%, 2%, 1%, 0.5%, 0.1%, 0.05%, and 0.01% Atmer-163. Sixty mm Petri dishes were then molded from these resin blends, and the growth of HEK-293 cells was observed in serum-free media (GIBCO CD-293A) on non-sterile parts. The growth of HEK-293 cells was achieved as described above in Example 3. Both untreated blends and corona blends were used to prepare Petri dishes. Attachment of cells was estimated by using crystal violet stain extraction and microscopic examination. More specifically, crystal violet stain was applied to the cells for five minutes and then rinsed with tap water. The retained stain was extracted in a solution of 1% Triton X-100 in $dH_2O$. The stain intensity was measured spectrophotometrically at 562 nm. The greater the retained stain, the greater the number of adherent cells, with results shown in FIG. 3. As can be seen, many of the corona-treated Atmer blends outperformed current products, such as CellBIND® in growing HEK-293 cells.

While the present invention has been disclosed by reference to the details of preferred embodiments, it is to be understood that the disclosure is intended as an illustrative rather than in a limiting sense, as it is contemplated that modifications will readily occur to those skilled in the art, within the spirit of the invention and the scope of the amended claims.

What is claimed is:

1. An apparatus for the culture of biological materials, the apparatus, comprising:
    a nonfibrous substrate for the attachment of biological materials, the substrate comprising a blend of polymer plastic resin and amphipathic alkylamine ethoxylate molecules; and
    cells adherent to a surface of the substrate;
    wherein the amphipathic alkylamine ethoxylate molecules comprise hydrophilic moieties and a hydrophobic region, the hydrophobic region being embedded within the polymer plastic resin of the substrate away from contact with the cells, and the hydrophilic moieties being exposed on the surface of the substrate.

2. The apparatus of claim 1 wherein the apparatus is produced by coating the polymer plastic resin with the amphipathic alkylamine ethoxylate molecules while the resin is in pellet form to make the blend prior to melting the resin for the purpose of molding the apparatus.

3. The apparatus of claim 1 wherein the apparatus is produced by compounding the polymer plastic resin with the amphipathic alkylamine ethoxylate molecules to form the blend prior to melting the resin for the purpose of molding the apparatus.

4. The apparatus of claim 1 wherein the plastic polymer of the substrate is chosen from polystyrene, polypropylene, glycol-modified polyethylene terephthalate (PETG), polyethylene terephthalate (PET), polycarbonate, or mixtures thereof.

5. The apparatus of claim 1 wherein the amphipathic molecules have been blended with the polymer plastic resin at a proportion of about 1% w/w.

6. The apparatus of claim 1 wherein he amphipathic molecules have been blended with the polymer plastic resin at a proportion of about 0.1% w/w.

7. The apparatus of claim 1 wherein the hydrophobic region is a chain of carbon linked atoms having a length between 10 to 30 carbon atoms.

8. The apparatus of claim 1 wherein the amphipathic molecules do not include fluorocompounds.

9. An apparatus for the culture of biological materials, the apparatus, comprising:
    a nonfibrous substrate for the attachment of biological materials, the substrate comprising a blend of polymer plastic resin and amphipathic alkylamine ethoxylate molecules, wherein the amphipathic alkylamine ethoxylate molecules comprise hydrophilic moieties and a hydrophobic region, the hydrophobic region being embedded within the polymer plastic resin of the substrate, and the hydrophilic moieties being exposed on the surface of the substrate, and the surface with exposed hydrophilic moieties having been treated with corona discharge or plasma discharge, and
    cells adherent to the surface of the substrate.

10. An apparatus for the culture of biological materials, the apparatus, comprising:
    a nonfibrous substrate for the attachment of biological materials, the substrate comprising a blend of polymer plastic resin and amphipathic alkylamine ethoxylate molecules, wherein the amphipathic alkylamine ethoxylate molecules comprise hydrophilic moieties and a hydrophobic region, the hydrophobic region being embedded within the polymer plastic resin of the substrate, and the hydrophilic moieties being exposed on the surface of the substrate, and the surface with exposed hydrophilic moieties having been coated with poly-D-lysine or collagen, and
    cells adherent to the surface of the substrate.

* * * * *

UNITED STATES PATENT AND TRADEMARK OFFICE
CERTIFICATE OF CORRECTION

PATENT NO. : 8,642,307 B2  
APPLICATION NO. : 11/420267  
DATED : February 4, 2014  
INVENTOR(S) : Granchelli et al.

Page 1 of 1

It is certified that error appears in the above-identified patent and that said Letters Patent is hereby corrected as shown below:

Title page, item (57):
Abstract, Lines 1-2 read "surface prepare" and should read --surface prepared--.

In the Specification:

Column 1,
Line 46 reads "mimic" and should read --mimics--.

Column 3,
Line 62 reads "An apparatus ..." and should read --Certain aspects of the present invention are directed to an apparatus ...--.

In the Claims:

Column 12,
Line 21 (Claim 6) reads "he" and should read --the--.

Signed and Sealed this  
First Day of July, 2014

Michelle K. Lee  
*Deputy Director of the United States Patent and Trademark Office*